United States Patent [19]

Kohmura et al.

[11] 4,267,133

[45] May 12, 1981

[54] MANUFACTURE OF DENTURE BASE

[75] Inventors: Tamotsu Kohmura, Anamushi; Jun-ichi Yoshimine, Kohama-nishi, Japan

[73] Assignee: Sankin Industry Co., Ltd., Osaka, Japan

[21] Appl. No.: 20,478

[22] Filed: Mar. 14, 1979

[30] Foreign Application Priority Data

Mar. 15, 1978 [JP] Japan .................................. 53-30459

[51] Int. Cl.³ .............................................. A61C 13/00
[52] U.S. Cl. ....................................... 264/18; 264/22; 433/168; 433/195; 433/199; 433/200
[58] Field of Search .................................... 264/16–20, 264/22; 32/2, 12, 15; 433/167, 168, 191, 195–196, 199–200

[56] References Cited

U.S. PATENT DOCUMENTS

| | | | |
|---|---|---|---|
| 2,498,368 | 2/1950 | Harrison | 264/17 |
| 2,886,890 | 5/1959 | Schnell | 264/16 |
| 3,638,312 | 2/1972 | Szwarc et al. | 32/15 |

FOREIGN PATENT DOCUMENTS

| | | |
|---|---|---|
| 940493 | 2/1956 | Fed. Rep. of Germany . |
| 883679 | 7/1943 | France . |
| 49-10887 | 3/1974 | Japan . |

*Primary Examiner*—Jeffery R. Thurlow
*Attorney, Agent, or Firm*—Oblon, Fisher, Spivak, McClelland & Maier

[57] ABSTRACT

A denture base is made of a photocuring resin compound by a process which includes polymerizing methacrylate and/or acrylate with the addition of a light sensitizer or a filler. Subsequent to a proper alignment of artificial teeth, the photo-curing or -hardening resin compound is hardened by exposure to light and artificial gingivae are formed by the same resin compound as above, followed by photocuring, thereby completing manufacture of the denture base.

Advantageously, the method disclosed herein facilitates markedly the manufacture of denture bases in comparison with conventional methods such as thermal polymerization and casting. The resulting denture bases show excellent properties.

19 Claims, No Drawings

MANUFACTURE OF DENTURE BASE

BACKGROUND OF THE INVENTION

1. Field of the Invention

This invention relates to the manufacture of denture bases, and more particularly to a method of manufacturing quality denture bases easily through the use of photocurable resin compounds. The present invention is also applicable to the manufacture of metallic denture bases, resinous denture bases, overall dentures and partial dentures.

2. Description of the Prior Art

Several ways of manufacturing denture bases are well knonw: (1) thermal polymerization wherein a mixture of polymer powder and liquid monomer is cast into a negative mold, as disclosed in W. German Pat. No. 940,493, Japanese Patent Publication 46/40108, etc.; (2) room temperature polymerization wherein a mixture of polymer powder, liquid monomer and a polymerization agent is cast into a negative mold, see, for example, W. German Pat. No. D 85578, Swiss Pat. No. 74466 and French Pat. No. 883679; and (3) injection molding wherein polymer pellets are heated and melted, for example, Japanese Patent Publication No. 42/4833.

The serious disadvantages of those conventional procedures, however, are that (a) manufacture of the negative mold in advance is indispensable, (b) procedures for casting or injection are laborious and require rather expensive facilities, (c) after hardening, removal of the mold is time- and labor-consuming, (d) polishing subsequent to removal of the mold is also indispensable, and (e) the resin tends to shrink and deform during the curing or hardening process with an accompanying decline in accuracy of the molding.

SUMMARY OF THE INVENTION

With the foregoing in mind, it is an object of the present invention to provide a highly effective and efficient method for manufacturing denture bases having a high degree of adaptability to the oral cavity, without any extraordinary amount of time and labor.

It is another object of the present invention to provide a method of manufacturing denture bases which employs a particular photo-curing type resin compound and particularly utilizes its photocuring properties.

Other objects of the present invention will become apparent from the following disclosure. The above-described primary object of the present invention is accomplished in the following manner. The gist of the present invention rests in a method comprising in sequence the steps of (a) applying thinly a photocuring type resin compound to a plaster mold coated with a mold release, mounting a metallic base thereon in the case of a metallic denture base and applying lightly the same resin compound as above, and curing the resin compound by exposure to actinic radiation, said photocuring type resin compound comprising polymerizable methacrylate and/or acrylate with addition of a light sensitizer and/or a filler; (b) applying the same resin compound thereto and photocuring after a proper alignment of artificial teeth; and (c) applying the same resin compound and photocuring after formation of artificial gingivae.

The photocuring type resin compound used in the practice of the present invention will first be described.

As is well known, requirements for dental resin material are generally as follows:

(1) The material is transparent or translucent per se and easy to dye and color so as to reproduce accurately the oral cavity structure;

(2) the material does not discolor or fade inside or outside the mouth after manufacture;

(3) it does not expand, shrink or deform during manufacture or in use;

(4) it assumes sufficient strength, elasticity and abrasion resistance to withstand everyday use;

(5) it is insoluble in and remains unaffected by the oral fluid;

(6) it does not pick up food residues and is as easy to clean as the mouth and teeth;

(7) it is tasteless, odorless, nontoxic and non-irritating to the oral cavity texture;

(8) the specific gravity is low and the heat conductivity is high;

(9) the softening point is much higher than the temperature of food; and

(10) when damaged, it is rather easy to repair. The present inventors, therefore, conducted an extensive search for the best photo-curing type resin material which fulfills all the requirements set forth above. The findings revealed that polymerizable methacrylates and/or acrylates were most desirable in meeting those requirements.

The following is a list of the raw materials useful for producing such a polymer, as are well known as photo-curing type resins.

[I] polyester polymethacrylates and/or polyester polyacrylates,

[II] polyol polymethacrylates and/or polyol polyacrylates,

[III] epoxy polymethacrylates and/or epoxy polyacrylates,

[IV] a reaction product of acrylic acid and/or methacrylic acid with a monoepoxide and an acid anhydride,

[V] monomethacrylates and/or monoacrylates which contain a carboxyl group in the molecule and have a boiling point of $\geq 250°$ C. at atmospheric pressure,

[VI] epoxy-terminated monomethacrylates and/or monoacrylates,

[VII] polyurethane polymethacrylates and/or polyurethane polyacrylates,

[VIII] polyamide methacrylates and/or polyamide acrylates,

[IX] the polymethacrylate and/or polyacrylate of the alcohol adduct of a phenol compound and an oxide compound, and

[X] monomethacrylate and/or monacrylate.

Those materials may be used solely, or in combination according to the intended use. It does not matter if a slight amount of a polymerization inhibitor still remains in the above-described polymerizable methacrylates and/or arcylates after manufacture or if a polymerization inhibitor less than 300 ppm is added thereto in order to enhance the storage stability of the resin system. Preferably, the light sensitizer for said polymerizable methacrylates and/or acrylates (referred to as "base resin material" hereinafter) is selected from among benzil benzoin methyl ether, benzoin ethyl ether, benzoin propyl ether, benzoin butyl ether, etc. Those materials may be used solely or in combination. Although the amount of the light sensitizer to be added is determined by the type of the base resin material, the curing rate, the compounding ratio of other additives (pigment, etc.) and so on, it is generally selected from a range from 0.2 to 10% by weight of the base resin material, preferably 0.5-8% by weight. It is also possible to promote curing through the utilization of a peroxide catalyst such as diaryl peroxides, e.g., benzoyl peroxide, hydroperoxides, dialkyl peroxides, diacyl peroxides and peroxy esters in addition to the light sensitizer and through utilization of the heat generated by actinic radiation. It is, however, to be noted that more than 2% by weight of the peroxide catalyst with respect to the base resin material may destroy storage stability of the photocuring resin material. Therefore, if it is desired to add the peroxide catalyst, its amount should be below 2% by weight.

The photocuring type resin compound used according to the present invention results from a uniform admixture and dissolution of the above described ingredients. A suitable plasticizer and a proper coloring agent may be further added thereto. In addition, a substituted phenol such as p-methoxyphenol or 2,6-di-tert-butyl-p-cresol may be added as a free radical polymerization inhibitor in order to enhance the storage stability of the compound.

In accordance with the present invention, the photocuring type resin compound is laid up and molded so as to manufacture the denture base. To this end the photocuring type resin compound should be in the form of paste or sheet for molding. According to the present invention, an organic or inorganic filler is mixed into the photocuring type resin compound. Exemplary organic fillers are water-soluble or insoluble polymers, in particular methacrylate polymers and/or acrylate polymers, polyvinyl acetate, polyvinyl alcohol, polyvinyl butyral, polystyrene, polyvinyl ether, polyvinyl pyrrolidone, copolymers of butadiene and acrylonitrile, polyamides, polyesters, vinylon, silicon resin, etc. and these fillers may be added at the level of 5-80% by weight based on the weight of the base resin material. One of satisfactory inorganic fillers is finely divided silicic anhydride (grain size: 7-40 m$\mu$), which is used desirably in the proportion of 0.5-50% by weight based on the base resin material. Other examples of the inorganic filler are glass fibers such as those of satin weave or plain weave, all of which are suitable for formulation of sheetlike photocuring type resin compounds. In other words, such a sheetlike photocuring type resin compound is easily obtainable as long as a glass fiber mat is impregnated with the base resin material with added light sensitizer and filler such as organic polymer and silicic anhydride. Without glass fiber as the filler, the base resin material may be put to use in the form of paste or sheet.

The manufacture of the denture base embodying the present invention will be now described in a stepwise manner.

[I] A plaster mold is made in accordance with an oral cavity impression and then installed on an articulator. Subsequently, in order to assist in the separation of the photocuring type resin compound from the plaster mold, the plaster mold is coated with a mold release such as aqueous sodium alginate solution, white vaseline and silicon oil and overlaid with a thin layer of the photocuring type resin compound. In the case of the sheetlike resin compound, the compound is applied and in the case of the pastelike compound it is laid up by spreading to form a thin layer. The compound is then irradiated with actinic radiation for photocuring. In the case of a metallic denture base, a metallic base is mounted thereon after the plaster mold is coated with the mold release and overlaid with the photocuring type resin compound. Then, the same photocuring type resin compound is applied thinly and cured by actinic radiation.

[II] On the cured resin compound there is further applied the same photocuring type resin compound to make a proper alignment of the artificial teeth, followed by exposure to actinic radiation for photocuring.

[III] Lastly, the same resin compound is applied thereto for the formation of artificial gingivae, and cured by irradiation.

If necessary, the surface of the resulting denture base is coated with the polymerizable methacrylate and/or acrylate in liquid phase including the light sensitizer and cured by exposure to light for surface-glazing purposes.

The photocuring procedure is carried through by utilization of actinic radiation of a wavelength of 3400°A or more. A mercury vapor lamp, a carbon arc lamp, an ultraviolet fluorescent lamp, a tungsten lamp, a xenon lamp, an argon glow lamp, a photographic lamp, solar rays, etc. may be used as the light source. The period of time needed for photocuring differs slightly dependent upon the type of the photocuring type resin compound (the base resin material and the compounding ratio of the light sensitizer, etc.), the intensity of actinic radiation, the thickness of the resin compound layer, etc. If the thickness of the resin compound is approximately 2 mm, the photocuring is almost completed within 60 seconds.

As noted earlier, the present invention eliminates the need for a negative mold and removal of the mold and thus reduces greatly labor and time for the manufacture of denture bases. In addition, the present invention provides a denture base highly adaptable to the affected part, with less or no distortion, shrinkage or deformation as experienced in the prior art thermal polymerization method. Since the present invention makes it possible to cure the photocuring type resin compound while confirming accurately position of the artificial teeth under visual observation, there is no likelihood that the artificial teeth will change in position as experienced in the prior art room-temperature casting method. The denture bases resulted from the present invention is further advantageous in that there exist no fins or gates, and the polishing operation is simple.

In the following disclosure, the present invention is explained in terms of its preferred embodiments, but not limited thereto, all "parts" are by weight, and "%" means % by weight for the convenience of explanation.

EXAMPLE 1

0.3 Part of benzoin methyl ether, 0.1 part of benzil, and 0.01 part of 2,6-di-tert-butyl-p-cresol were mixed and dissolved into 20 parts of "ARONIX M-7100" (oligoarylate) available from Toa Synthetic Chemistry Co., and 0.02 part of coloring agent and 7 parts of ultrafine silicic anhydride ("AEROSIL R-972" from Nippon Aerosil Co.) were further added thereto and kneaded by means of a kneader for preparation of the pasty photocuring type resin compound A.

When the resin compound A is light-cured by a 100 W high voltage mercury lamp (Ushio Electric Co.), the photocuring rate, the cured bending strength, the modulus of bending elasticity, the surface hardness, the water absorbing capacity, and the solubility of the resin compound were measured. The photocuring rate was measured in terms of the period of time required for complete curing of the 2 mm thick compound when the distance from the irradiation source was 10 cm. The bending strength, the modulus of bending elasticity and the tensile strength were measured for a 3×10×60 mm³ sample of the photocuring compound, with an Instron universal testing machine, a bending point-to-point distance of 50 mm or a pulling rate of 3 mm/min. The surface hardness was measured in terms of Rockwell superficial hardness on scale 15 W. The water absorbing capacity and the solubility were tested pursuant to JIS (Japanese Industrial Standard) T-6501. The findings are listed in Table 1. For comparison the same test was carried out on a sample of the commercially available thermal polymerization type resin for denture base use, as seen from Table 1.

TABLE 1

|  | Compound A of the present invention | Commercially available resin |
|---|---|---|
| Photocuring rate (sec.) | 20 | — |
| Bending strength (kg/cm²) | 800 | 805 |
| Modulus of bending elasticity (kg/cm²) | $2.8 \times 10^4$ | $2.4 \times 10^4$ |
| Surface hardness (Hz) | 80 | 80 |
| Water absorbing capability (mg/cm²) | 0.4 | 0.5 |
| Solubility (mg/cm²) | 0.01 | 0.01 |

A $-\sqrt{567}$ metallic denture base was made by utilization of the above described photocuring type resin material A and the above described high voltage mercury lamp. Moldability of the photocuring type resin compound A was extremely good and manufacture of the denture base was simple, time-saving and highly efficient. The steps and time required for manufacturing the denture bases are listed in Table 2, in comparison with the commercially available thermal polymerization resin.

TABLE 2

| Commercially available resin | | Compound A of the present invention | |
|---|---|---|---|
| Step | Time | Step | Time |
| Artificial teeth alignment and formation of artificial gingivae | 60 min | | |
| Flask sink (twice) | 60 min | Artificial teeth alignment and formation of artificial gingivae photocuring (photocuring is 30 sec. long for each application of material) | 60 min |
| Waxing resin injection | 30 min | | |
| Thermal polymerization | 60 min | | |
| Plaster mold separation polishing | 30 min | | |
| Total time | 4 hrs. | Total time | 1 hr. |

The fit of the denture bases resulted from the photocuring type resin compound A is very excellent. Clinical examination after a year showed no abnormality of the denture bases.

EXAMPLE 2

0.5 Part of benzil and 0.01 part of 2,6-di-tert-butyl-p-cresol were dissolved into 15 parts of 2,2-bis [4-(3-methacryloxy-2-hydroxypropoxy)phenyl] propane and 5 parts of triethylene glycol dimethacrylate, followed by the addition of 40 parts of powder of methacrylate-styrene copolymer and a slight amount of coloring agent. The mixture was then kneaded by means of a kneader for preparation of the pasty photocuring type resin material B.

Moldability of the resulting resin compound B was excellent and the photocuring rate was 60 seconds under the same conditions as in Example 1.

EXAMPLE 3

0.5 Parts of benzoin methyl ether and 0.01 part of 2,6-di-tert-butyl-p-cresol were dissolved into 20 parts of "ARONIX M-7100", supra, for preparation of the photocuring type resin compound C. The resin compound C was liquid with a viscosity of 10000 cps at 25° C. and the photocuring rate was less than 10 seconds.

The denture base in Example 1 was coated with the resin compound C and then cured by exposure to light, which resulted in an excellent luster.

EXAMPLE 4

2% of benzil and 20% of "AEROSIL R-972" were added to "ARONIX M-7100", supra, followed by kneading. A satin-weave glass fiber cloth (Nittobo Co.) was impregnated with the above mixture to obtain a 2 mm thick photocuring type resin compound D in the form of sheet. The photocuring rate of compound D was 20 seconds. The compound D was used as a base material and the pasty photocuring type resin compound A in Example 1 was utilized for manufacture of a $\sqrt{567}$ partial denture base. The glazing was accomplished by the liquid photocuring type resin material C prepared in Example 3.

The resulting denture base showed excellent fit to the affected part and clinical examination after a year revealed no abnormality of the denture base nor of the affected part.

We claim:
1. A method for manufacturing a denture base, comprising in sequence the steps of:
   (a) applying thinly a photocuring resin compound to a plaster mold coated with a mold release agent and curing the resin compound by uniform exposure thereof to actinic radiation, said photocuring resin compound comprising a polymerizable methacrylate and/or acrylate with the addition of a light sensitizer or a filler;
   (b) applying the above defined photocuring resin compound to the layer photocured in the step (a), after the affixing and alignment of artificial teeth, then curing the resin compound by uniformm exposure to actinic radiation; and
   (c) applying the above defined photocuring resin compound to the layer photocured during the step (b), after the formation of artificial gingavae, then curing the resin compound by uniform exposure to actinic radiation.
2. A method for manufacturing a denture base, comprising in sequence the steps of:
   (a) applying thinly a photocuring resin compound to a plaster mold coated with a mold release agent, mounting a metallic base thereon, applying thinly said resin compound thereto, and curing the resin compound by exposure to actinic radiation, said photocuring resin compound comprising a polymerizable methacrylate and/or acrylate with added light sensitizer and/or filler;

(b) applying the above defined photocuring resin compound to the layer photocured during the step (a), after the affixing said alignment of artificial teeth, curing the resin compound by uniform exposure to actinic radiation; and (c) applying the above defined photocuring resin compound to the layer photocured during the step (b), after the formation of artificial gingavae, then curing the resin compound by uniform exposure to actinic radiation.

3. The method of claim 1 or 2 wherein said light sensitizer is selected from the group of benzil and benzoin ethers.

4. The method of claim 3 wherein said light sensitizer within said photocuring type resin compound occurs in a proportion of 0.2-10% by weight with respect to said polymerizable methacrylate and/or acrylate.

5. The method of claim 1 or 2 wherein said filler within said photocuring type resin compound is a water-soluble or insoluble organic polymer.

6. The method of claim 5 wherein said organic polymer within said photocuring type resin compound occurs in a proportion of 5-80% by weight with respect to said polymerizable methacrylate and/or acrylate.

7. The method of claim 1 or 2 wherein said filler within said photocuring type resin compound is inorganic.

8. The method of claim 7 wherein said inorganic filler is ultrafine silicic anhydride with a particle size of 7-40 mµ.

9. The method of claim 8 wherein said ultrafine silicic anhydride is present in a proportion of 0.5-50% by weight with respect to said polymerizable methacrylate and/or acrylate.

10. The method of claim 7 wherein said inorganic filler within said photocuring type resin compound is glass fiber.

11. The method of claim 1 or 2 wherein said filler within said photocuring type resin compound includes an organic polymer and ultrafine silicic anhydride.

12. The method of claim 10 wherein said photocuring resin compound is used to impregnate said glass fiber.

13. The method of claim 1 or 2 wherein said photocuring resin compound is moldable in the form of paste.

14. The method of claim 1 or 2 wherein said photocuring resin compound is moldable in the form of sheet.

15. The method of claim 1 or 2 wherein said photocuring resin compound contains a peroxide catalyst as well as the light sensitizer.

16. The method of claim 15 wherein said peroxide catalyst within said photocuring resin compound is diaryl peroxide.

17. The method of claim 15 wherein the quanity of said peroxide catalyst within said photocuring resin compound is 0.01-2% by weight with respect to said polymerizable methacrylate and/or acrylate.

18. The method of claim 1 or 2 wherein said photocuring is effected by exposure to rays of actinic radiation of a wavelength longer than 3400 Å.

19. The method according to claim 18 wherein curing by actinic retiation is completed within 60 seconds when the thickness of said photocuring type resin compound is 2 mm.

* * * * *